(12) United States Patent
Lawter et al.

(10) Patent No.: US 6,893,665 B2
(45) Date of Patent: May 17, 2005

(54) FORMULATIONS FOR TREATING OR PREVENTING MUCOSITIS

(75) Inventors: James Ronald Lawter, Yardley, PA (US); Stephen J. Comiskey, Doylestown, PA (US)

(73) Assignee: Orapharma, Inc., Warminster, PA (US)

( * ) Notice: Subject to any disclaimer, the term of this patent is extended or adjusted under 35 U.S.C. 154(b) by 0 days.

(21) Appl. No.: 10/007,197

(22) Filed: Dec. 4, 2001

(65) Prior Publication Data

US 2002/0045604 A1 Apr. 18, 2002

Related U.S. Application Data

(63) Continuation of application No. 09/661,836, filed on Sep. 14, 2000.
(60) Provisional application No. 60/153,892, filed on Sep. 14, 1999.

(51) Int. Cl.$^7$ .............................. A61K 7/16; A61K 9/16; A61K 9/127; A61K 9/20
(52) U.S. Cl. ........................ 424/489; 424/49; 424/484; 424/450
(58) Field of Search ................................ 514/901, 152; 424/489, 49, 464, 450, 484

(56) References Cited

U.S. PATENT DOCUMENTS

| | | | |
|---|---|---|---|
| 3,966,808 A | | 6/1976 | Luciano |
| 4,081,527 A | * | 3/1978 | Armstrong et al. |
| 4,961,926 A | | 10/1990 | Gabrilove |
| 5,082,653 A | | 1/1992 | Pan et al. |
| 5,102,870 A | | 4/1992 | Florine et al. |
| 5,254,338 A | * | 10/1993 | Sakai et al. |
| 5,284,963 A | | 2/1994 | Sum et al. |
| 5,328,902 A | | 7/1994 | Sum et al. |
| 5,386,041 A | | 1/1995 | Sum et al. |
| 5,401,729 A | | 3/1995 | Sum et al. |
| 5,420,272 A | | 5/1995 | Sum et al. |
| 5,430,162 A | | 7/1995 | Sum et al. |
| 5,545,668 A | | 8/1996 | Skubitz et al. |
| 5,635,489 A | | 6/1997 | Haley |
| 5,827,840 A | | 10/1998 | Ramamurthy et al. |
| 5,886,175 A | | 3/1999 | Sum et al. |
| 5,945,089 A | | 8/1999 | Libin |
| 5,981,499 A | | 11/1999 | Hau |
| 6,025,326 A | | 2/2000 | Steinberg et al. |
| 6,451,771 B1 | * | 9/2002 | Henderson et al. |

FOREIGN PATENT DOCUMENTS

| | | |
|---|---|---|
| WO | WO 94/27579 A1 | 12/1994 |
| WO | WO 98/18610 A1 | 5/1998 |
| WO | WO 99/22703 A1 | 5/1999 |
| WO | WO 99/45910 A2 | 9/1999 |
| WO | WO 00/07601 A1 | 2/2000 |

OTHER PUBLICATIONS

Barker, et al., "Oral care with vancomycin paste for reduction in incidence of alpha–hemolytic streptococcal sepsis," J Pediatr Hermatol Oncol 17(2):151–55 (1995).

Cartee, et al., "Evaluation of GM–CSF mouthwash for prevention of chemotherapy–induced mucositis: a randomized, double–blind, dose–ranging study," *Cytokine* 7(5):471–7 (1994).

Chi, et al., "Effect of granulocyte–macrophage colony–stimulating factor on oral mucositis in head and neck cancer patients after cisplatin, fluorouracil, anc leucovorin chemotherapy," *J. Clin. Oncol.* 13(10):2620–28 (1995).

Cutler & Schubert, "Patient factors affecting *Helicbacter pylon* eradication with triple therapy," *American Journal of Gastroenterology* 88:(4):505–509 (1993).

Epstein & Wong, "The efficacy of sucralfate suspension in the prevention of oral mucositis due to radiation therapy," *Int. J. Radiat. Oncol. Biol. Phys.* 28(3):693–98 (1994).

Epstein, et al., "Benzydamine hydrochloride in prevention and management of pain in oral mucositis associated with radiation therapy," *Oral Surg. Oral Med. Oral Pathol.* 62(2):145–8 (1986).

Epstein, et al., "Prevention of oral mucositis in radiation therapy: a controlled study with benzydamine hydrochloride rinse," *Int. J. Radiation Oncology Biol. Phys.* 16(6):1571–5 (1989).

*Essentials of Medicinal Chemistry* John Wiley and Sons, Inc., pp 512–517 (1976).

Facchini, et al., "Attivita di flunoxaprofene per uso topico nelle vaginiti aspecifiche, Confronto con meclociclina solfosalicilato," *Minerva Ginecologica.* 41(12):609–614 (1989).

Ferretti, et al., "Control of oral mucositis and candidiasis in marrow transplantation: a prospective, double–blind trial of chlorhexidine digluconate oral rinse," *Bone Marrow Transplant* 3(5):483–93 (1990).

Foote, et al., "Randomized trial of a chlorhexidine mouthwash for alleviation of radiation–induced mucositis," *J. Clin Oncol.* 12(12):2630–33 (1994).

(Continued)

Primary Examiner—Edward J. Webman
(74) Attorney, Agent, or Firm—Clark & Elbing LLP

(57) ABSTRACT

Mucositis is treated and/or prevented by administrating to a patient a formulation comprising a tetracycline that is poorly absorbed from the gastro-intestinal tract. The tetracycline may be in the form of a pharmaceutically acceptable salt or a base. The formulations may optionally also contain an antifungal agent to prevent fungal overgrowth due to reduction in the normal oral flora by the tetracycline. Such compositions have the advantage of treating the entire gastro-intestinal tract since the active ingredient is not removed from the tract via absorption. Further, such compositions minimize systemic exposure and accompanying side effects.

11 Claims, No Drawings

OTHER PUBLICATIONS

Franceschi, et al., "Solitary J–pouch ulcer causing pouchitis–like syndrome," *Diseases of the Colon and Rectum* 29(8):515–517 (1986).

Loprinzi, et al., "Alleviation of cytoxic therapy–induced normal tissue damage," *Sem. Oncol.* 22(2) Suppl. 3:95–97 (1995).

Mitscher, et al., "Quinolone antimicrobial agents 1. Versatile new synthesis of 1–alkyl–1, 4–dihydro–4–oxo–3–quinolinecarboxylic acids," *J. Med. Chem.* 21(5):485–9 (1978).

Rothwell & Spektor, "Palliation of radiation–related mucositis," *Special Care in Denistry* 10(1):21–25 (1990).

Schenk, et al., "Controlled local delivery of tetracycline HCl in the treatment of periimplant mucosal hyperplasia and mucositis," *Clinical Oral Implants Research* 8(5):427–433 (1997).

Sonis, 1993b, "Oral Complications in Cancer Therapy," In: *Principles and Practice of Oncology*, De Vitta et al., eds., pp. 2385–2394 (J. B. Lippincott, Philadelphia).

*Special Care in Dentistry* Jan.–Feb, pp. 21–25 (1990).

Spijkervet, et al., "Chlorhexidine inactivation by saliva," *Oral Surg. Oral Med. Oral Pathol.* 69(4):444–49 (1990).

Verdi, et al., "A double–blind, randomized, placebo–controlled, crossover trial of pentoxifyline for the prevention of chemotherapy–induced oral mucositis," *Oral Surg. Oral Med. Oral Pathol. Oral Radiol. Endod*, 80(1):36–42 (1995).

Weisdorf, et al., "Oropharyngeal mucositis complicating bone marrow transplantation: prognostic factors and the effect of chlorhexidine mouth rinse," *Bone Marrow Transplant* 4(1):89–95 (1989).

* cited by examiner

FORMULATIONS FOR TREATING OR PREVENTING MUCOSITIS

CROSS-REFERENCE TO RELATED APPLICATIONS

This application is a continuation of pending prior application U.S. Ser. No. 09/661,836 filed Sep. 14, 2000, which claims priority to U.S. Ser. No. 60/153,892 filed Sep. 14, 1999.

FIELD OF THE INVENTION

The present application relates generally to formulations containing a tetracycline that are useful for treating or preventing mucositis.

BACKGROUND OF THE INVENTION

Mucositis is a dose-limiting side effect of cancer therapy and bone marrow transplantation and is not adequately managed by current treatment (Sonis, 1993a, "Oral Complications," in: *Cancer Medicine*, pp. 2381–2388, Holand et al.; Eds., Lea and Febiger, Philadelphia; Sonis, 1993b, "Oral Complications in Cancer Therapy," In: *Principles and Practice of Oncology*, pp. 2385–2394, De Vitta et al., Eds., J. B. Lippincott, Philadelphia). Oral mucositis is found in almost 100% of patients receiving radiotherapy for head and neck tumors, in about 40% of patients receiving chemotherapy, and in about 90% of children with leukemia (Sonis, 1993b, supra). Complications related to oral mucositis, though varying in the different patient populations, generally include pain, poor oral intake with consequent dehydration and weight loss, and systemic infection with organisms originating in the oral cavity leading to septicemia (Sonis, 1993b; U.S. Pat. No. 6,025,326 to Steinberg et al.). In addition to the oral cavity, mucositis may also affect other parts of the gastro-intestinal tract.

A variety of approaches to the treatment of oral mucositis and associated oral infections have been tested with limited success. For example, the use of an allopurinol mouthwash, an oral sucralfate slurry, and pentoxifyline were reported in preliminary studies to result in a decrease in mucositis. Subsequent randomized and controlled studies, however, have failed to demonstrate any benefit from treatment with these agents (Loprinzi et al., 1995, *Sem. Oncol.* 22 *Suppl.* 3): 95–97; Epstein & Wong, 1994, Int. J Radiation Oncology Biol. Phys. 28:693–698; Verdi et al., 1995, Oral Surg. Oral Med. Oral Pathol. Oral Radiol. Endod. 80:36–42).

Other therapies have been directed at decreasing oral flora and the extent of oral infections. Systemic treatment with G- and GM-CSF has been shown to result in a decreased incidence of oral mucositis, presumably by allowing for more rapid neutrophil recovery and thus an improved ability to combat infection, although it has been postulated that the CSFs may have a more direct effect on the oral mucosa (Chi et al., 1995, *J. Clin. Oncol.* 13:2620–2628). Nonetheless, in one study, GM-CSF was reported to exacerbate mucositis (Cartee et al., 1994, *Cytokine* 7:741–477). Benzydamine hydrochloride, a nonsteroidal drug with analgesic and antimicrobial properties, has been studied both in patients undergoing radiation therapy and in patients receiving intra-arterial chemotherapy (Epstein et al., 1986, *Oral Surg. Oral Med. Oral Pathol.* 62:145–148; Epstein et al., 1989, *Int. J Radiation Oncology Biol. Phys.* 16:1571–1575) but without much success.

Chlorhexidine, an antimicrobial mouth rinse, has also been used extensively in the treatment and prevention of oral mucositis (Ferretti et al., 1990, *Bone Marrow Transplan.* 3:483–493; Weisdorf et al., 1989, *Bone Marrow Transplan.* 4:89–95). It has been noted, however, that the efficacy of chlorhexidine is significantly decreased in saliva, and that this compound is relatively ineffective against the Gram negative bacteria that tend to colonize the oral cavity in patients undergoing radiation therapy (Spijkervet et al., 1990, *Oral Surg. Oral Med. Oral Pathol.* 69:444–449). In addition, at least one study has shown that the use of chlorhexidine may be detrimental and result in a higher incidence of mucositis (Foote et al., 1994, *J. Clin Oncol.* 12:2630–2633).

Several studies have shown that the use of a vancomycin paste and antibiotic lozenges containing polymixin B, tobramycin and amphotericin B in patients undergoing myelosuppresive chemotherapy or radiation therapy can result in a decrease in oral mucositis and in the incidence of sepsis due to alpha hemolytic streptococci (Barker et al., 1995, *J Ped. Hem. Oncol.* 17:151–155; Spijkervet et al., 1991, In: *Irradiation Mucositis*, Munksgaard Press, pp. 43–50).

Other methods of treating or preventing mucositis using a variety of formulations have been reported. U.S. Pat. No. 5,545,668 to Skubitz et al. describes formulations containing glutamine. U.S. Pat. No. 5,635,489 to Haley, U.S. Pat. No. 4,961,926 to Gabrilove, and U.S. Pat. No. 5,102,870 to Florine et al., describe treatments using formulations containing growth factors or stimulating factors. Formulations contain antimicrobial peptides such as protegrin as the effective ingredient have also been described by U.S. Pat. No. 6,025,326 to Steinberg et. al. A triclosan formulation for treating mucositis was reported in U.S. Pat. No. 5,945,089 to Libin.

Despite the clear need for therapeutic agents to treat oral mucositis, none of the treatments provide significant long-term relief or decrease the severity or duration of mucositis. As a result, there is no standard treatment for oral mucositis.

Rothwell and Spektor (Special Care in Dentistry, Jan.–Feb 1990, pages 21–25) have shown that patients to whom an oral rinse containing tetracycline, diphenhydramine, nystatin, and hydrocortisone was administered developed less severe mucositis than patients receiving a control rinse. The concentrations of the active ingredients in this study were tetracycline, 500 mg; nystatin, 1,200,000 U; hydrocortisone, 100 mg; and diphenhydramine elixir, 10 ml made up to a total volume of 250 ml. The tetracycline was unstable in solution with the other ingredients and was therefore administered in a separate solution.

WO 99/45910 by Sonis and Fey describes a method for treating and preventing mucositis by administering a non-steroidal anti-inflammatory (NSAID), an inflammatory cytokine inhibitor, or a mast cell inhibitor and second different therapeutic agent which is an NSAID, an inflammatory cytokine inhibitor, a mast cell inhibitor, a matrix metalloproteinase (MMP) inhibitor or a nitric oxide inhibitor. There are further claims where the MMP inhibitor is a tetracycline. These complex mixtures appear to reduce mucositis in animal models but the relative efficacies of the different active agents and effective dosages are unclear. Most of the active ingredients have side effects if absorbed systemically at effective dosages. Only the compositions containing the tetracyclines appear to significantly reduce the symptoms of the mucositis.

It is therefore an object of the present invention to provide a method and composition to decrease the duration and/or severity of mucositis by administering a composition containing a tetracycline as the active ingredient which is not absorbed systemically.

It is a further object of the present invention to provide a treatment that is safe, efficacious and easy for the patient to use.

SUMMARY OF THE INVENTION

Mucositis is treated and/or prevented by administrating to a patient a formulation comprising a tetracycline that is poorly absorbed from the gastro-intestinal tract. The tetracycline may be in the form of a pharmaceutically acceptable salt or a base. The formulations may optionally also contain an antifungal agent to prevent fungal overgrowth due to reduction in the normal oral flora by the tetracycline. Such compositions have the advantage of treating the entire gastrointestinal tract since the active ingredient is not removed from the tract via absorption. Further, such compositions minimize systemic exposure and accompanying side effects.

DETAILED DESCRIPTION OF THE INVENTION

I. Topical Tetracycline Formulations

Topical formulations for treating mucositis have been developed. These include as the active ingredient to treat the mucositis a tetracycline type compound that is poorly absorbed when administered orally or topically to the mucosa, a carrier which may be a solvent or suspending agent and include excipients modifying the viscosity, taste, stability, adherence or release properties, and optionally an anti-fungal agent.

A. Tetracyclines

As used herein, tetracyclines include compounds that may or may not have antibiotic activity. The tetracyclines described herein are those which are poorly absorbed when administered orally. Compounds which have bioavailibilities of about 10% or less are considered to be poorly absorbed. The tetracyclines are known to have pharmacological activities such as matrix metalloproteinase, nitric oxide synthetase and caspase inhibition that are independent of their antibiotic properties. These activities may be important in the treatment and prevention of mucositis. It is known that these pharmacological activities may be associated with tetracyclines that do not have significant antibiotic properties.

Tetracyclines are defined by the following structure:

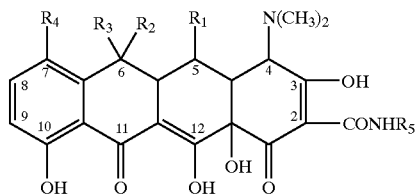

wherein $R_1$–$R_5$ may be a hydrogen atom, a halogen atom, a hydroxyl group, or any other organic composition comprising from 1–8 carbon atoms and optionally include a heteroatom such as nitrogen, oxygen, in linear, branched, or cyclic structural formats.

A wide range and diversity of embodiments within the definition of the above structure as are described within *Essentials of Medicinal Chemistry* John Wiley and Sons, Inc., 1976, pages 512–517, the text of which is incorporated by reference herein. Preferably $R_1$ and $R_2$ are hydrogen or a hydroxyl group; $R_3$ is hydrogen or a methyl group; $R_4$ is a hydrogen atom, a halogen, or a nitrogen containing entity; and $R_5$ is a hydrogen atom, or nitrogen containing ring structure. The commonly known tetracycline analogues and derivatives include the following: oxytetracycline; chlortetracycline; demeclocycline; doxycycline; minocycline; rolitetracycline; lymecycline; sancycline; methacycline; apicycline; clomocycline; guamecycline; meglucycline; mepylcline; penimepicycline; pipacycline; etocycline, penimocycline, and meclocycline.

Tetracycline derivatives that can be used as described herein, include tetracycline derivatives modified at positions 1 through 4 and 10 through 12, although these modifications may result in reduction in antibiotic properties, according to Mitscher, et al., J. Med. Chem. 21(5), 485–489 (1978). The configuration of the 4 carbon is important to the antibiotic properties of the tetracyclines. For the antibiotic tetracyclines, carbon 4 is in the S configuration. The 4-epimers of the tetracyclines, which have the R configuration at the 4 carbon, have significantly reduced antibiotic activity. Other such non-antibiotic tetracycline analogs include the 4-de(dimethylamino) derivatives of the tetracyclines listed in the above paragraph. Specific examples include: 6-demethyl -6-deoxy-4-dedimethylaminotetracycline; 6-demethyl-6-deoxy-4-dedimethylamino -7-dimethylaminotetracycline; 6-demethyl-6-deoxy-4-dedimethylamino -7-chloro-tetracycline; 4-hydroxy-4-dedimethylaminotetracycline; 6a-deoxy-5-hydroxy-4-dedimethylaminotetracycline; 4-dedimethylamino-5-oxytetracycline, and 4-dedimethylamino -11-hydroxy-12a-deoxytetracycline. Further examples of tetracyclines with reduced antibiotic activity include 6-α-benzylthiomethylenetetracycline, 6-fluoro-6-demethyltetracycline, and 11α-chlorotetracycline.

Other tetracycline related compounds that can be used as described herein are the 9-((substituted)amido)tetracyclines. The latter include the compounds described in U.S. Pat. Nos. 5,886,175, 5,284,963, 5,328,902, 5,386,041, 5,401,729, 5,420,272, and 5,430,162.

Preferred poorly absorbed tetracyclines include compounds of the following structure:

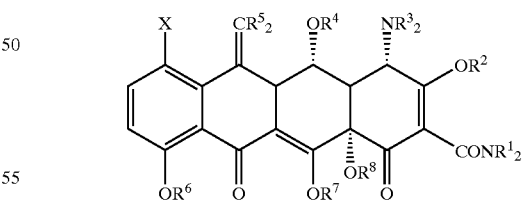

wherein $R^1$, $R^2$, $R^3$, $R^4$, $R^5$, $R^6$, $R^7$, and $R^8$ can be H, C1–C3 alkyl, pheny, aryl groups; and wherein X is an H, alkyl, alkoxy, phenoxy, aryloxy, amino group, amide, acyl, and halo group; and pharmaceutically acceptable salts thereof.

The most preferred compound of this general structure is wherein $R^1$, $R^2$, $R^4$, $R^5$, $R^6$, $R^7$, and $R^8$ are H;

wherein $R^3$ is $CH_3$; and wherein X is a chloro group. The generic name for this compound is meclocycline.

The preparation of meclocycline and its analogs and derivatives are known. For example, U.S. Pat. No. 3,966,808 to Luciano discloses methods for manufacturing 6-methylenetetracyclines.

B. Pharmaceutically Acceptable Carriers

The formulations may be prepared as a liquid, semi-solid, or solid containing an amount of a poorly absorbed tetracycline that is effective to treat or prevent mucositis. Generally, these compositions contain about 0.001 to 1 mg/mL of the tetracycline.

The compositions are topically administered to the oral mucosa and then swallowed. Formulation types suitable for this route of administration include liquids applied as mouthrinses; solid dosage forms that may dissolve in the mouth; and semisolids that may be applied to oral cavity surfaces.

Tetracyclines in general may not be sufficiently stable in aqueous solutions to permit formulations with long shelf lives at room temperature, i.e. a year or more, to be prepared. Stability of the tetracyclines varies greatly with structure. However, solids for re-constitution as aqueous based solutions prepared either by the patient or by a pharmacist prior to administration to the patient can be used, even for the least stable members of the class. Also polyvalent metal ion complexes may be prepared that are stable in contact with water at room temperature for two years or more. Examples are the calcium and magnesium complexes. These complexes may be suspensions in water.

The stability of the tetracyclines in aqueous solutions is pH dependent. Procedures for choosing the optimum pH and buffering agents are well known. Other factors that affect stability in solution are also well known. For example, antioxidants may be added to reduce the rate of degradation due to oxidation.

In addition to the tetracycline and antifungal agents, an aqueous liquid preparation may contain buffers, surfactants, humectants, preservatives, flavorings, stabilizers (including antioxidants), colorants, and other additives used in preparations administered into the oral cavity.

The compositions used as mouthwashes preferably should have a pH of 3.5 to 8. A pH of 4 to 6.5 is most preferable. A preparation having a pH of less than about 4 would be likely to cause a stinging sensation. Furthermore, the preparations having a higher pH are often unpleasant to use. The active agents need not be in solution to be effective. The active agents may be present wholly or in part as suspensions in aqueous solutions used as carriers to provide liquid compositions.

The preparations are buffered as necessary to provide the appropriate pH. Appropriate buffer systems include citrate, acetate, tromethamine and benzoate systems. However, any buffer system commonly used for preparing medicinal compositions would be appropriate. While the vehicle used generally is primarily water, other vehicles may be present such as alcohols, glycols (polyethylene glycol or polypropylene glycol are examples), glycerin, and the like may be used to solubilize the active agents. Surfactants may include anionic, nonionic, amphoteric and cationic surfactants, which are known in the art as appropriate ingredients for mouthwashes.

Liquid formulations may contain additional components to improve the effectiveness of the product. For example, component(s) may be added to increase viscosity to provide improved retention on the surfaces of the oral cavity. Suitable viscosity increasing agents include carboxyalkyl, hydroxyalkyl, and hydroxyalkyl alkyl celluloses, xanthan gum, carageenan, alginates, pectins, guar gum, polyvinylpyrolidone, and gellan gums. High viscosity formulations may cause nausea in chemotherapy and radiation patients and are therefore not preferred. Gellan gums are preferred as viscosity modifying agents since aqueous solutions containing certain gellan gums may be prepared so that they will experience an increase in viscosity upon contact with electrolytes. Saliva contains electrolytes that will interact with such a gellan containing solution so as to increase their viscosity.

Flavorings used in the mouthrinse art such as peppermint, citrus flavorings, berry flavorings, vanilla, cinnamon, and sweeteners, either natural or artificial, may be used. Flavorings that are known to increase salivary electrolyte concentrations may be added to increase the magnitude of the viscosity change. The increased viscosity will promote retention of the solutions in the oral cavity and provide greater effectiveness due to increased contact time with the affected tissues.

In order to improve the patient acceptability, it is desirable to add an appropriate coloring and/or flavoring material. Any pharmaceutically acceptable coloring or flavoring material may be used.

Additional antimicrobial preservatives may be component of the formulation in cases where it is necessary to inhibit microbial growth. Suitable preservatives include, but are not limited to the alkyl parabens, bernzoic acid, and benzyl alcohol. The quantity of preservative may be determined by conducting standard antimicrobial preservative effectiveness tests such as that described in the United States Pharmacopoeia.

Suitable solid dosage forms include powders or tablets that are designed for constitution as solutions by dissolution or suspension in a liquid vehicle and include troches, pastilles or lozenges that dissolve slowly in the mouth. For convenience of use, solids designed to be dissolved to prepare a liquid dosage form prior to administration preferably are rapidly dissolving. Technologies to produce rapidly dissolving solids are well known in the art. These include spray-drying, freeze-drying, particle size reduction and optimizing the pH of the dissolution medium.

The solubilities of tetracyclines are a complex function of pH since they have several ionizable functional groups. Tetracyclines generally have a minimum in their pH-solubility curves between a pH of 3 and 6. The Tate of dissolution of acidic salts may be increased by dissolving in a neutral to basic buffer. Dispersal of such salts may optimally be done at low pH.

C. Other Active Agents

Other medicinal agents may be added for purposes of alleviating other undesirable conditions in the mouth. Such agents may include, for example, local anesthetics, antibacterial agents, and emollients, as well as anti-fungal agents.

Anti-Fungal Agents

Antibiotic tetracyclines applied topically in the oral cavity may reduce the number of susceptible flora to such an extent that competitive conditions that hold non-susceptible organisms in check may not be effective. In particular, fungi, which are not susceptible to tetracyclines, may increase drastically in number. To avoid this, an antifungal agent may be added to the composition. Examples of antifungal agents that have been shown to be effective in preventing or treating fungal overgrowth are nystatin and clotrimazole. These agents may be added to a liquid tetracycline dosage form as a powder to form a suspension. The approved dosage for Clotrimazole, 10 mg is three times a day for mucositis. The approved dosage of Nystatin is 200,000 to 400,000 units, 4 to 5 times a day for up to 14 days in pastilles.

Examples of local anesthetics are lidocaine and a eutectic mixture of lidocaine and prilocaine. Lidocaine is administered in solution at a concentration of 2%, at a dose of 15 ml, at intervals of not less than three hours. The eutectic mixture is equimolar, administered at a total concentration of up to 5%. Either could be incorporated in an aerosol at similar doses.

II. Methods of Treatment

Methods of using the formulations disclosed herein generally involve applying the formulations topically to mucosal surfaces of the oral cavity and gastro-intestinal tract. One to six applications per day beginning 24 hours before chemotherapy or radiation until conclusion of treatment are made. The typical volume of a mouthwash would be between 5–15 ml.

Therapy is continued for as long as the patient is receiving radiation or chemotherapy.

The present invention will be further understood by reference to the following non-limiting examples.

Methods and Materials

The following animal model was used to demonstrate the effectiveness of the poorly absorbed tetracyclines in treating mucositis.

Hamsters were randomly assigned to treatment groups with eight (8) animals per group. Each group was treated either with a drug solution or a control, water.

Animals were dosed three times a day for 22 days. The first dose was applied on day —1. Either a solution of the drug or water alone was applied in a volume of 0.1 ml three times per day.

Mucositis was induced by acute radiation exposure of the check pouch. A single dose of radiation (35 Gy/dose) was administered to all animals on Day 0. Prior to irradiation, animals were anesthetized with an intraperiotoneal injection of sodium pentobarbital (80 mg/kg) and the left buccal pouch was everted, fixed and isolated using a lead shield.

Beginning on day 6 and continuing every other day up to day 28, the cheek pouch was photographed. On days that photographs were taken, prior to the first dosing of the day, the animals were anesthetized using an inhalation anesthetic and the left cheek pouch of each animal was rinsed vigorously with sterile water to remove residual food debris or foreign contamination and blotted dry with a gauze sponge. The appearance of the cheek pouch was scored visually by comparison to a validated photographic scale, ranging from 0 for normal to 5 for severe ulceration (clinical scoring). In descriptive terms, this scale is defined as follows:

| Score | Description |
|---|---|
| 0 | Pouch completely healthy. No erythema or vasodilatation |
| 1 | Light to severe erythema and vasodilatation. No erosion of mucosa |
| 2 | Severe erythema and vasodilatation. Erosion of superficial aspects of mucosa leaving denuded areas. Decreased stippling of mucosa. |
| 3 | Formation of off-white ulcers in one or more places. Ulcers may have a yellow/gray color due to pseudomembrane formation. Cumulative size of ulcers up to ¼ of the pouch surface. Severe erythema and vasodilatation. |
| 4 | Cumulative size of ulcers ¼ to ½ of the pouch surface. Loss of pliability. Severe erythema and vasodilatation. |
| 5 | Virtually all of pouch is ulcerated. Loss of pliability (pouch can only partially be extracted from mouth). |

A score of 1–2 represents mild stage of the disease, whereas a score of 3–5 indicates moderate to severe mucositis.

These examples demonstrate that the tetracycline compositions significantly reduce the severity of mucositis when administered topically to the oral mucosa. Further they show that meclocycline which is poorly absorbed is as effective as a well absorbed tetracycline or tetracycline HO.

EXAMPLE 1

Treatment with Meclocycline Sulfosalicylate (0.1 mg/ml)

Eight hamsters were treated as described above with 0.1 mL of aqueous solutions containing 0.1 mg/mL meclocycline sulfosalicylate. The solution was prepared by dissolving meclocycline in an aqueous solution of a tromethamine buffer. Significantly lower scores were found in the group treated with the meclocycline solution than a group of hamsters treated with a placebo control consisting of the solution without meclocycline. Relative to the control group, the group treated with meclocycline had a reduction of more than 75% in the number of animal days with scores of 3 or more.

EXAMPLE 2

Treatment with Tetracycline Hydrochloride (0.1 mg/ml)

Eight hamsters were treated as described above with 0.1 mL of aqueous solution containing 0.1 mg/ml tetracycline hydrochloride. Significantly lower scores were found in the group treated with the tetracycline solution than a group of hamsters treated with a placebo control consisting of the solution without tetracycline. Relative to the control group, the group treated with tetracycline had a reduction of more than 75% in the number of animal days with scores of 3 or more.

These examples demonstrate that the tetracycline compositions significantly reduce the severity of mucositis when administered topically to the oral mucosa. Further they show that meclocycline which is poorly absorbed is as effective as a well absorbed tetracycline.

EXAMPLE 3

Freeze-Dried Meclocycline Gellan Gum Formulations

Meclocycline hydrochloride powder formed by freeze drying in bulk is added to a solution containing gellan gum at a concentration of 0.5 mg/mL. The tetracycline concentration is 0.1 mg/mL. The solution also contains methyl and propyl parabens as antimicrobial preservatives at concentrations of 0.18% and 0.02%, respectively and tromethamine buffer.

EXAMPLE 4

Miconized Meclocycline Gellan Gum Buffered Formulations

Meclocycline hydrochloride powder formed by micronization is added to a solution containing gellan gum at a concentration of 0.5 mg/mL. The tetracycline concentration is 0.05 mg/mL. The solution also contains methyl and propyl parabens as antimicrobial preservatives at concentrations of 0.18% and 0.02%, respectively and tromethamine buffer.

EXAMPLE 5

Spray-Dried Meclocycline Gellan Gum Formulation

Meclocycline hydrochloride powder formed by spray drying is added to a solution containing gellan gum at a concentration of 0.5 mg/mL. The tetracycline concentration is 0.01 mg/mL. The solution also contains methyl and propyl parabens as antimicrobial preservatives at concentrations of 0.18% and 0.02%, respectively and tromethamine buffer.

EXAMPLE 6

Micronized Meclocycline Buffered Formulation

Meclocycline sulfosalicylate powder formed by micronization is added to water. The suspension is added to a second solution containing a tromethamine buffer to form a mixture with a pH of approximately 8.

EXAMPLE 7

Meclocyline Coated Pellets

Pellets comprised of an inner core of tromethamine buffer and a coating of meclocycline hydrochloride embedded in methyl cellulose is added to water to form a mouth rinse. The concentration of the tetracycline in the solution is 0.1 mg/mL.

EXAMPLE 8

Meclocycline Tablets

A rapidly disintegrating tablet containing meclocycline sulfosalicylate is added to water. The tablet disintegrates and a second tablet containing a buffer is added to the solution to raise the pH so that the tetracycline rapidly dissolves.

EXAMPLE 9

Meclocycline Calcium Complex Suspension

A meclocyline calcium complex suspension is formed by addition of the hydrochloride salt of meclocycline to a solution of calcium lactate, which has been made basic, by the addition of sodium hydroxide. The solution also contained methyl and propyl parabens as antimicrobial preservative and EDTA and sodium bisulfite as antioxidants. The solutions were sparged with nitrogen to remove dissolved oxygen prior to addition of the sodium bisulfite. The mixture is deaerated.

EXAMPLE 10

Meclocycline Suspension

A suspension of meclocycline sulfosalicylate is formed by addition of micronized drug to an aqueous solution containing 0.5% gellan gum and methyl and propyl parabens as antimicrobial preservative.

EXAMPLE 11

Meclocycline Sulfosalicylate Suspension

A suspension of meclocycline sulfosalicylate is formed by addition of micronized drug to a unit dose quantity of an aqueous solution containing 0.5% gellan gum. No antimicrobial preservative is required since the formulation is used immediately after preparation.

EXAMPLE 12

Aeorosolized Micronized Meclocycline

A metered dose aerosol container is filled with micronized meclocycline sulfosalicylate and a non-FREON™ propellant. The container is equipped with a valve for delivering 500 mcg per actuation. The container is also equipped with a tube for directing the aerosol to the interior of the mouth.

EXAMPLE 13

Meclocycline Oral Rinse Solution

A powder containing meclocycline hydrochloride and buffer to promote rapid dissolution is prepared by granulation. The powder is dissolved in water to form an oral rinse solution containing 0.05 mg/mL meclocycline.

EXAMPLE 14

Effervescent Tablet Containing Meclocycline Formulation

An effervescent tablet containing meclocycline sulfosalicylate and sodium bicarbonate. The tablet is dissolved in water to form an oral rinse solution containing 0.1 mg/mL meclocycline.

Those skilled in the art will recognize, or be able to ascertain using no more than routine experimentation, many equivalents to the specific embodiments of the present application described herein. Such equivalents are intended to be encompassed by the following claims.

We claim:

1. A pharmaceutical composition for treating or preventing mucositis comprising an effective amount of a poorly absorbed tetracycline which is not tetracycline or meclocycline in a carrier for topical administration to the mucosa, wherein the carrier for topical administration to the mucosa of the oral cavity and gastro-intestinal tract is selected from the group consisting of a mouthwash, lozenge, tablet, paste and gel and further wherein the tetracycline is in the form of a polyvalent metal ion complex.

2. The composition of claim 1 wherein the tetracycline is selected based on poor oral absorption from the group consisting of tetracyclines defined by the following structure:

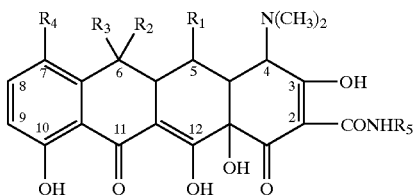

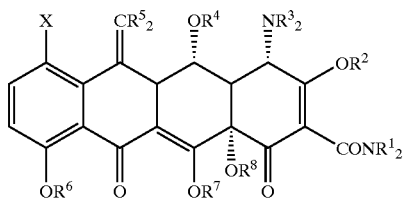

wherein $R_1$–$R_5$ are hydrogen atoms, halogen atoms, hydroxyl groups, or C1–8 groups which optionally include a heteroatom such as nitrogen, oxygen, in linear, branched, or cyclic structural formats.

3. The composition of claim 2 wherein $R_1$ and $R_2$ are hydrogen or a hydroxyl group; $R_3$ is hydrogen or a methyl group; $R_4$ is a hydrogen atom, a halogen, or a nitrogen containing entity; and $R_5$ is a hydrogen atom, or nitrogen containing ring structure.

4. The composition of claim 2 wherein the tetracycline is modified by substitution of H at carbon 9 by a substituted amido group.

5. The composition of claim 2 wherein the tetracycline is modified at any of positions 1 through 4 and 10 through 12.

6. The composition of claim 2 having the following structure:

wherein $R^1$, $R^2$, $R^3$, $R^4$, $R^5$, $R^6$, $R^7$, and $R^8$ can be H, C1–C3 alkyl, phenyl, and aryl group; and wherein X is an H, alkyl, alkoxy, phenoxy, aryloxy, amino group, amide, acyl, and halo group; and pharmaceutically acceptable salts thereof.

7. The composition of claim 1 wherein the carrier for topical administration comprises the tetracycline coated onto or encapsulated into a carrier selected from the group consisting of powders, pellets, microcapsules, liposomes, and emulsions.

8. The composition of claim 7 wherein the tetracycline is formulated as a dry powder.

9. The composition of claim 1 wherein less than 10% of the tetracycline is absorbed into the systemic circulation when topically administered to the mouth and then swallowed.

10. The composition of claim 1 wherein the polyvalent metal ion is calcium or magnesium.

11. The composition of claim 1 wherein the tetracycline is formulated to be topically administered to the mucosa as an aerosol.

* * * * *

UNITED STATES PATENT AND TRADEMARK OFFICE
CERTIFICATE OF CORRECTION

PATENT NO. : 6,893,665 B2
DATED : May 17, 2005
INVENTOR(S) : Lawter et al.

It is certified that error appears in the above-identified patent and that said Letters Patent is hereby corrected as shown below:

Column 4,
Line 11, replace "mepyclcline" with -- mepicycline --; and
Line 11, replace "etocycline" with -- cetocycline --.

Column 6,
Line 34, replace "bernzoic" with -- benzoic --; and
Line 11, replace "Tate" with -- rate --.

Column 9,
Line 9, replace "Miconzied" with -- Micronzied --; and
Line 43, replace "is added" with -- are added --.

Column 12,
Line 12, replace "group;" with -- groups; --.

Signed and Sealed this

Nineteenth Day of July, 2005

JON W. DUDAS
*Director of the United States Patent and Trademark Office*

Disclaimer

6,893,665 — James Ronald Lawter, Yardley, PA (US); and Stephen J. Comiskey, Doylestown, PA (US). FORMULATIONS FOR TREATING OR PREVENTING MUCOSITIS. Patent dated May 17, 2005. Disclaimer filed November 8, 2012, by the assignee, Orapharma, Inc. Hereby enters this disclaimer to claims 1-11 of said patent.

Hereby enters this disclaimer to claims 1-11 of said patent.

(*Official Gazette, December 18, 2012*)